(12) United States Patent
Chandorkar et al.

(10) Patent No.: US 9,724,353 B2
(45) Date of Patent: Aug. 8, 2017

(54) METHODS FOR TREATING INTRAPULMONARY INFECTIONS

(71) Applicant: Calixa Therapeutics, Inc., Lexington, MA (US)

(72) Inventors: Gurudatt A. Chandorkar, Waltham, MA (US); Jennifer A. Huntington, Reading, MA (US); Tara Parsons, Hanover, MA (US); Obiamiwe C. Umeh, Acton, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/512,608

(22) Filed: Oct. 13, 2014

(65) Prior Publication Data

US 2015/0045338 A1 Feb. 12, 2015

Related U.S. Application Data

(63) Continuation of application No. 13/607,138, filed on Sep. 7, 2012, now abandoned.

(60) Provisional application No. 61/532,914, filed on Sep. 9, 2011, provisional application No. 61/657,386, filed on Jun. 8, 2012.

(51) Int. Cl.

| | |
|---|---|
| *A61K 31/431* | (2006.01) |
| *A61P 31/04* | (2006.01) |
| *A61K 31/43* | (2006.01) |
| *A61P 31/00* | (2006.01) |
| *A61K 31/546* | (2006.01) |
| *A61K 9/00* | (2006.01) |

(52) U.S. Cl.
CPC ............ *A61K 31/546* (2013.01); *A61K 9/007* (2013.01); *A61K 9/0019* (2013.01); *A61K 31/431* (2013.01)

(58) Field of Classification Search
CPC combination set(s) only.
See application file for complete search history.

(56) References Cited

U.S. PATENT DOCUMENTS

| | | | |
|---|---|---|---|
| 4,200,575 A | 4/1980 | Numata | |
| 4,246,405 A | 1/1981 | Takaya et al. | |
| 4,255,431 A | 3/1981 | Junggren | |
| 4,264,597 A | 4/1981 | Hashimoto et al. | |
| 4,267,176 A | 5/1981 | Kamiya et al. | |
| 4,268,509 A | 5/1981 | Teraji et al. | |
| 4,284,631 A | 8/1981 | Takaya et al. | |
| 4,291,031 A | 9/1981 | Takaya et al. | |
| 4,298,529 A | 11/1981 | Ueda et al. | |
| 4,299,829 A | 11/1981 | Kamiya et al. | |
| 4,305,937 A | 12/1981 | Kamiya et al. | |
| 4,327,093 A | 4/1982 | Ueda et al. | |
| 4,331,665 A | 5/1982 | Teraji et al. | |
| 4,332,798 A | 6/1982 | Teraji et al. | |
| 4,332,800 A | 6/1982 | Teraji et al. | |
| 4,336,253 A | 6/1982 | Lunn | |
| 4,338,313 A | 7/1982 | Teraji et al. | |
| 4,339,449 A | 7/1982 | Hashimoto | |
| 4,363,807 A | 12/1982 | Takaya et al. | |
| 4,367,228 A | 1/1983 | Takaya et al. | |
| 4,368,325 A | 1/1983 | Ueda | |
| 4,369,312 A | 1/1983 | Hashimoto et al. | |
| 4,370,326 A | 1/1983 | Takaya et al. | |
| 4,390,534 A | 6/1983 | Teraji et al. | |
| 4,394,384 A | 7/1983 | Takaya et al. | |
| 4,402,955 A | 9/1983 | Lunn | |
| 4,405,617 A | 9/1983 | Takaya et al. | |
| 4,407,798 A | 10/1983 | Kamiya et al. | |
| 4,409,214 A | 10/1983 | Takaya et al. | |
| 4,409,215 A | 10/1983 | Takaya et al. | |
| 4,409,217 A | 10/1983 | Takaya et al. | |
| 4,416,879 A | 11/1983 | Takaya et al. | |
| 4,420,477 A | 12/1983 | Takaya et al. | |
| 4,423,213 A | 12/1983 | Takaya et al. | |
| 4,425,340 A | 1/1984 | Teraji et al. | |
| 4,425,341 A | 1/1984 | Takaya et al. | |
| 4,427,677 A | 1/1984 | Takaya et al. | |
| 4,430,499 A | 2/1984 | Wheeler | |
| 4,431,642 A | 2/1984 | Teraji et al. | |
| 4,436,912 A | 3/1984 | Wheeler | |
| 4,438,113 A | 3/1984 | Takaya et al. | |
| 4,443,443 A | 4/1984 | Ueda et al. | |
| 4,443,444 A | 4/1984 | Takaya et al. | |
| 4,447,429 A | 5/1984 | Teraji et al. | |
| 4,450,270 A | 5/1984 | Lunn | |

(Continued)

FOREIGN PATENT DOCUMENTS

| | | |
|---|---|---|
| CN | 99100092.7 | 12/1999 |
| CN | 200810238479.7 | 5/2009 |

(Continued)

OTHER PUBLICATIONS

Abstract for Moulds et al.,. Impact of characterized resistance mechanisms on the susceptibility of Pseudomonas aeruginosa to CXA-101. 5oth Annual Interscience Conference on Antimicrobial Agents and Chemotherapy (ICAAC 2010); Sep. 12-15, 2010. Poster C1-1415; This poster is obtainable at: http://www.cubisl.com/downloads/Moulds.PP. ICAAC_2010.1mpact_of_resis_mech_on_ suscep_of_P_aeruginosa_to_CXA_JNS.pdf.

Abstract for Umeh et al., A double-blind, randomized, phase 2 study to compare the safety and efficacy of intravenous CXA-101 and intravenous ceflazidime in complicated urinary tract infection. 50th AnnualInterscience Conference on Antimicrobial Agents and Chemotherapy (ICAAC 2010); Sep. 12-15, 2010. Poster L1-361A; This poster is obtainable at: http://www.cubisl.com/downloads/Umeh_ ICAAC2010_08144v2.pdf.

(Continued)

*Primary Examiner* — Kathrien Cruz
(74) *Attorney, Agent, or Firm* — Dechert LLP

(57) ABSTRACT

This disclosure relates to the treatment of intrapulmonary bacterial infections, including treatment of nosocomial pneumonia lung infections with pharmaceutical compositions containing the cephalosporin ceftolozane.

13 Claims, 7 Drawing Sheets

(56) References Cited

U.S. PATENT DOCUMENTS

| | | |
|---|---|---|
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn |
| 4,515,788 A | 5/1985 | Takaya et al. |
| 4,521,413 A | 6/1985 | Teraji et al. |
| 4,546,101 A | 10/1985 | Takaya et al. |
| 4,550,102 A | 10/1985 | Teraji et al. |
| 4,559,334 A | 12/1985 | Takaya et al. |
| 4,563,449 A | 1/1986 | Teraji et al. |
| 4,577,014 A | 3/1986 | Lunn |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,751,295 A | 6/1988 | Oka et al. |
| 4,761,410 A | 8/1988 | Takaya et al. |
| 4,764,606 A | 8/1988 | Imai et al. |
| 4,808,711 A | 2/1989 | Shimizu et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes |
| 5,162,520 A | 11/1992 | Takaya et al. |
| 5,173,485 A | 12/1992 | Sakane et al. |
| 5,187,160 A | 2/1993 | Sakane et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei |
| 5,637,580 A | 6/1997 | White |
| 5,646,139 A | 7/1997 | White |
| 5,648,346 A | 7/1997 | White |
| 5,656,623 A | 8/1997 | White |
| 5,661,144 A | 8/1997 | Tsushima et al. |
| 5,663,163 A | 9/1997 | Takaya et al. |
| 5,763,603 A | 6/1998 | Trickes |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,800,621 B2 | 10/2004 | Nishitani et al. |
| 6,878,686 B2 | 4/2005 | Marquess et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,279,458 B2 | 10/2007 | Fatheree et al. |
| 7,332,471 B2 | 2/2008 | Fatheree et al. |
| 7,341,993 B2 | 3/2008 | Fatherlee et al. |
| 7,384,928 B2 | 6/2008 | Nishitani |
| 7,417,143 B2 | 8/2008 | Gnanaprakasam et al. |
| 7,553,962 B2 | 6/2009 | Fatherlee et al. |
| 7,601,690 B2 | 10/2009 | Fatherlee et al. |
| 7,612,037 B2 | 11/2009 | Fatherlee et al. |
| 7,649,080 B2 | 1/2010 | Fatherlee et al. |
| 7,655,621 B2 | 2/2010 | Fatherlee et al. |
| 7,728,127 B2 | 6/2010 | Fatheree et al. |
| 8,476,245 B2 | 7/2013 | Pourmotabbed et al. |
| 2002/0115650 A1 | 8/2002 | Glinka |
| 2003/0130173 A1 | 7/2003 | Fatheree et al. |
| 2006/0241017 A1 | 10/2006 | Chandran |
| 2006/0287244 A1 | 12/2006 | Chandran |
| 2007/0219191 A1 | 9/2007 | Nishitani et al. |
| 2009/0137460 A1 | 5/2009 | Marquess et al. |
| 2011/0136763 A1 | 6/2011 | Xia et al. |
| 2014/0262868 A1 | 9/2014 | Terracciano |
| 2014/0274989 A1 | 9/2014 | Terracciano |
| 2014/0274990 A1 | 9/2014 | Terracciano |
| 2014/0274991 A1 | 9/2014 | Damour |
| 2014/0274992 A1 | 9/2014 | Damour |
| 2014/0274993 A1 | 9/2014 | Terracciano |
| 2014/0274994 A1 | 9/2014 | Damour |
| 2014/0274995 A1 | 9/2014 | Zhou |
| 2014/0274996 A1 | 9/2014 | Damour |
| 2014/0274997 A1 | 9/2014 | Zhou et al. |
| 2014/0274998 A1 | 9/2014 | Terracciano |
| 2014/0275000 A1 | 9/2014 | Damour |
| 2014/0303136 A1 | 10/2014 | Terracciano |
| 2014/0309205 A1 | 10/2014 | Terracciano |

FOREIGN PATENT DOCUMENTS

| | | |
|---|---|---|
| CN | 200910169647.6 | 4/2010 |
| CN | 201010557481.8 | 4/2011 |
| CN | 201110061045.6 | 3/2012 |
| EP | 0047977 A2 | 3/1982 |
| EP | 111934 A2 | 6/1984 |
| EP | 0137442 A2 | 4/1985 |

(56) References Cited

FOREIGN PATENT DOCUMENTS

| EP | 84111744 | | 4/1985 |
|---|---|---|---|
| EP | 84306866 | | 4/1985 |
| EP | 318767 | A2 | 6/1989 |
| EP | 0664117 | A1 | 7/1995 |
| EP | 0678095 | A1 | 10/1995 |
| EP | 711774 | A1 | 5/1996 |
| EP | 1134222 | B1 | 4/2005 |
| EP | 1554287 | B1 | 7/2005 |
| EP | 1587497 | A1 | 10/2005 |
| EP | 1711178 | A1 | 10/2006 |
| EP | 1799209 | A1 | 6/2007 |
| EP | 1919449 | A2 | 5/2008 |
| EP | 1959933 | B1 | 8/2008 |
| EP | 2015755 | | 1/2009 |
| EP | 2063869 | A2 | 6/2009 |
| EP | 2086570 | | 8/2009 |
| EP | 2120880 | A1 | 11/2009 |
| EP | 2136844 | | 12/2009 |
| EP | 2203177 | | 7/2010 |
| EP | 2280713 | | 9/2011 |
| EP | 1154770 | | 11/2011 |
| EP | 2440523 | | 4/2012 |
| JP | 62103092 | A | 5/1987 |
| JP | 62158290 | A | 7/1987 |
| JP | 63051388 | A | 3/1988 |
| JP | 63051389 | A | 3/1988 |
| JP | 2088582 | A | 3/1990 |
| JP | 2117678 | A | 5/1990 |
| JP | 4288086 | A | 10/1992 |
| JP | 5222058 | A | 8/1993 |
| JP | 6056848 | A | 3/1994 |
| JP | 6128268 | A | 5/1994 |
| JP | 2005162670 | A | 6/2005 |
| WO | WO 99/28308 | | 6/1999 |
| WO | WO 99/64049 | | 12/1999 |
| WO | 0004915 | A1 | 2/2000 |
| WO | WO 03/078440 | | 9/2003 |
| WO | WO 2004/048551 | | 6/2004 |
| WO | WO 2005/005436 | | 1/2005 |
| WO | WO 2009/049086 | | 4/2009 |
| WO | WO 2009/105782 | | 8/2009 |
| WO | 2013036783 | A2 | 3/2013 |

OTHER PUBLICATIONS

Abstract for Brown et al. Activity profile of CXA-101 and CXA-101/tazobactam against target gram-positive and gram-negative pathogens. 49th Annual Interscience Conference on Antimicrobial Agents and Chemotherapy (ICAAC 2009); Sep. 12-15, 2009. Poster F1-1986; This poster is obtainable at: http://www.eurofins.com/media/767069/Finai%20F1-1986.pdf.

Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); Sep. 12-15, 2009. Poster F1-1998; This poster is obtainable at: http://www.eurofins.com/media/767072/Finai%20F1-1998.pdf.

Abstract for Brown et al.. Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Craig et al.. In vivo activity of CXA-101 plus a 2:1, 4:1, or 8:1 ratio of tazobactam against various Enterobacteriaceae producing Extended-spectrum bela-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against Pseudomonas aeruginosa and other Enterobacteriaceae in the thighs of neutropenic mice. 49th AnnualInterscience Conference on Antimicrobial Agents and Chemotherapy (ICAAC 2009); Sep. 12-15, 2009. Poster F1-2002.

Abstract for Ge et al., CXA-101 population PK analysis and Monte Carlo simulation for PKIPD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK study of CXA-101 in combination with tazobactam in dogs after intravenous administration. 49th AnnualInterscience Conference on Antimicrobial Agents and Chemotherapy (ICAAC 2009); Sep. 12-15, 2009. Poster F1-2001.

Abstract for Ge et al., PK and safety of CXA-101, a new anti-pseudomonal cephalosporin, in healthy adult subjects after single intravenous dosing. 49th AnnualInterscience Conference on Antimicrobial Agents and Chemotherapy (ICAAC 2009); Sep. 12-15, 2009. Poster F1-2004.

Abstract for Giske et al., CXA-101 has high activity against clinical isolates of Pseudomonas aeruginosa including ceftazidime-resistant isolates. 49th Annual Interscience Conference on Antimicrobial Agents and Chemotherapy (ICAAC 2009); Sep. 12-15, 2009. Poster F1-1988.

Abstract for Jacqueline et al. FIG Index determination of CXA-101/tazobactam in combination with amikacin, aztreonam, meropenem, levofloxacin, and tigecycline against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1995.

Abstract for Jacqueline et al. In vitro assessment using lime-kill curves of CXA-101/Iazobactam against *Escherichia coli*, Klebsiella pneumoniae, and Pseudomonas aeruginosa strains. 49th Annual lnterscience Conference on Antimicrobial Agents and Chemotherapy (ICAAC 2009); Sep. 12-15, 2009. Poster F1-1996.

Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/lazobactam. 49th Annual lnterscience Conference on Antimicrobial Agents and Chemotherapy (ICAAC 2009); Sep. 12-15, 2009. Poster F1-2000.

Abstract for Juan et al., Oliver A. Activity of the new cephalosporin CXA-101 against carbapenem-resistant Pseudomonas aeruginosa isolates from a Spanish multicenter study. 49th Annual lnterscience Conference on Antimicrobial Agents and Chemotherapy (ICAAC 2009); Sep. 12-15, 2009. Poster F1-1987.

Abstract for Maya et al. Affinity of the new cephalosporin CXA-101 to penicillin-binding proteins of Pseudomonas aeruginosa. 49th Annual lnterscience Conference on Antimicrobial Agents and Chemotherapy (ICAAC 2009); Sep. 12-15, 2009.

Abstract for Riera et al. Activity of the new cephalosporin CXA-101 against biofilms of relevant P. aeruginosa phenotypes in cystic fibrosis chronic respiratory infection: mucoid and hypermulable strains. 49th Annual Interscience Conference on Antimicrobial Agents and Chemotherapy (ICAAC 2009); Sep. 12-15, 2009. Poster F1-1990.

Abstract for Brown et al. Effect of various testing parameters on the activity of CXA-101 by broth microdilution. 48th AnnualInterscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http:l/www.eurofins.com/media/694469/CXA%20F1-357%20parameter%20v6.pdf.

Abstract for Brown et al. Activity profile of CXA-101 against gram-positive and gram-negative pathogens by broth and agar dilution. 48th AnnualInterscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixa%20F1-354%20brolh%20agar%20v6.pdf.

Abstract for Zamorano et al. Activity of the new cephalosporin CXA-101 against P. aeruginosa isolates from chronically infected cystic fibrosis patients. 49th Annual lnterscience Conference on Antimicrobial Agents and Chemotherapy (ICAAC 2009); Sep. 12-15, 2009. Poster F1-1991.

(56) References Cited

OTHER PUBLICATIONS

Abstract for Tilelman et al. Activity of CXA-101 plus tazobactam against ESBL-producing *E. coli* and K. pneumoniae. 49th Annual Interscience Conference on Antimicrobial Agents and Chemotherapy (ICAAC 2009); Sep. 12-15, 2009. Poster F1-1993.
Abstract for Sader et al., Activity of the novel cephalosporin CXA-101 tested in combination with tazobactam against cephalosporin-resistant Enterobacteriaceae, P. aeruginosa and B. fragilis. 49th Annual Interscience Conference on Antimicrobial Agents and Chemotherapy (ICAAC 2009); Sep. 12-15, 2009. Poster F1-1992; This poster is obtainable at: http://www.jmilabs.com/dala/posters/ICAAC2009/F1-1992.pdf.
Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358%201k%20mbc%20v5.pdf.
Abstract for Livermore et al., Warner M. Activity of cephalosporin CXA-101 vs. P. aeruginosa. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk!webc/HPAwebFile/HPAweb_C/1225354148015.
Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk!webc/HPAwebFile/HPAweb_C/1225354148047.
Abstract for Sader et al., Activity of the Novel Antimicrobial Ceftolozane/Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/dala/posters/IDWeek2012/846.pdf.
Abstract for Walkty et al. In Vitro Activity of Ceflolozane!Tazobactam (CXA-201) versus Pseudomonas aeruginosa Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https:l/idsa.confex.com/idsa/2012/webprogram/Handoul/id509/POSTER202_1616.pdf.
Abstract for Miller et al., Safety and Pharmacokinetics of Intravenous Ceflolozane/lazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobial Agents and Chemotherapy (ICAAC 2012); Sep. 9-12, 2012. Poster A-641.
Abstract for Sader et al., Activity of the Novel Antimicrobial Ceflolozane!Tazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199.
Abstract for Soon et al., In vitro Pharmacodynamics of CXA-201 (Ceflolozane!Tazobactam) against -lactamase Producing *Eschericia coli*. 52nd Annual Interscience Conference on Antimicrobial Agents and Chemotherapy (ICAAC 2012); Sep. 9-12, 2012. Poster E-201.
Abstract for Zhanel et al., In vitro Activity of Ceflolozane/lazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.
Abstract for Chandorkar et al. Intrapulmonary penetration of CXA-201 and Piperacillin/lazobactam in healthy adult subjects. 22nd Annual Meeting of the European Congress of Clinical Microbiology (ECCMID 2012); Mar. 31-Apr. 3, 2012. Poster P1627.
Abstract for Sader et al. Activity of Novel Antimicrobial CXA-201 Tested Against Contemporary Clininical Strains from European Hospitals. 22nd Annual Meeting of the European Congress of Clinical Microbiology (ECCMID 2012); Mar. 31-Apr. 3, 2012. Poster P1446.
Abstract for Snydman et al., Activity of Ceflolozane!Tazobactam CXA-201 against 270 recent isolates from the bacteroides group. 22nd Annual Meeting of the European Congress of Clinical Microbiology (ECCMID 2012); Mar. 31-Apr. 3, 2012. Poster; This poster is obtainable at: hftp://www.escmid.org/escmid_library/online_lecture_library/?search=1&current_page=1&search_term=snydman.
Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.
Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster 81-589.
Abstract for Killian et al. An Equivalency Study of a Sensititre Dried MIG Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.
Abstract for Maya et al. Pan-JI-lactam resistance development in P. aeruginosa clinical strains: molecular mechanisms. PBPs profiles and binding affinities. 51st Annual Interscience Conference on Antimicrobial Agents and Chemotherapy (ICAAC 2011); Sep. 17-20, 2011. Poster C1-619.
Abstract for Hershberger et al. CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.
Abstract for Miller et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.
Abstract for Fenneteau et al. Population PKIPD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/defaull/files/webforrn/posters/ACOP2011%20-%20Dosing%20Strategies%20of%20CXA-101%20and%20Taz%20in%20cUTI%20Patients.pdf.
Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.
Abstract for Bulik et al. In vivo Efficacy of Human Simulated CXA-101 ± Tazobactam versus Piperacillin-Tazobactam against Phenotypically Diverse Gram-negative Organisms. ICAAC 2010. Poster A1-1381; This poster is obtainable at: http://www.cubisl.com/downloads/Bulik_PP_ICAAC_201O_in_vivo_CXA-101_vs_TZP_against_gram_neg.pdf.
Abstract for Cabot et al. Activity of CXA-101 Against a Large Collection of P. aeruginosa Blood Stream Isolates Overexpressing AmpC and the Major Efflux Pumps. 50th Annual Interscience Conference on Antimicrobial Agents and Chemotherapy (ICAAC 2010); Sep. 12-15, 2010. Poster E-816.
Abstract for Jacqueline. Assessment of the in vivo Activity of CXA-101 in a Murine Model of Pseudomonas aeruginosa Pneumonia: Comparison with Ceftazidime and Piperacillin-Tazobactam.

(56) References Cited

OTHER PUBLICATIONS

5oth Annual Interscience Conference on Antimicrobial Agents and Chemotherapy (ICAAC 2010); Sep. 12-15, 2010. Poster B-1401.
Abstract for Marier et al. Pharmacokinetics of a novel antipseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.
Takeda, Shinobu, et al. "In vitro and in vivo activities of a new cephalosporin, FR264205, against Pseudomonas aeruginosa." Antimicrobial agents and chemotherapy 51.3 (2007): 826-830.
Sader, Helio S., et al. "Antimicrobial Activity of CXA-101, a Novel Cephalosporin Tested in Combination with Tazobactam against Enterobacteriaceae, Pseudomonas aeruginosa and Bacteroides fragilis Strains Having Various Resistance Phenotypes." Antimicrobial agents and chemotherapy (2011).
Cubist (Cubist Annoucnes Positive Results from Two Phase 2 Trials, CSA-201 and CDAD Program, Jun. 2011, pp. 1-5).
Bulik et al. "In Vitro Potency of CXA-101, a Novel Cephalosporin, against Pseudomonas aeruginosa." 47th Annual Meeting of the Infectious Diseases Society (IDSA 2009); Oct. 29-Nov. 1, 2009. Poster 209.
Livermore et al. Chequerboard titrations of cephalosporin CXA-101 and tazobactam vs. beta-lactamase producing Enterobacteriaceae. 49th Annual lnterscience Conference on Antimicrobial Agents and Chemotherapy (ICAAC 2009); Sep. 12-15, 2009. Poster F1-1994.
Moya et al. Activity of CXA-101 against Pseudomonas aeruginosa beta-lactam resistance mechanisms: ampD, ampDh2, ampDh2, dacB, and oprD mutations. 49th Annual lnterscience Conference on Antimicrobial Agents and Chemotherapy (ICAAC 2009); Sep. 12-15, 2009. Poster F1-1989.
Soon et al. A Novel Mathematical Modeling Approach to Characterize the Pharmacodynamics of Ceflolozane/Tazobactam, a betalactam & beta-lactamase Inhibitor Combination. 52nd Annual Interscience Conference on Antimicrobial Agents and Chemotherapy (ICAAC 2012); Sep. 9-12, 2012. Oral Presentation A-1762.
Miller et al. CXA-201 dose selection based on probability of target attainment and drug exposure in subjects with varying degrees of renal impairment. ICAAC 2011. Oral Presentation A-1099.
Steenbergen et al. Potency of CXA-101 Tazobactam for Pathogens from ICU and non-ICU Correlated to Probability of Pharmacokinetic/ Pharmacodynamic (PKIPD) Target Attainment. ICAAC 2011. Oral Presentation A-1689.
Hatano et al. In vivo Anti-Pseudomonas Aeruginosa Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.
Strayer et al. "Pharmacodynamics of piperacillin alone and in combination with tazobactam against piperacillin-resistant and -susceptible organisms in an in vitro model of infection." Antimicrob. Agents Chemother. vol. 38, No. 10, pp. 2351-2356.
Bush, K., et al. "Kinetic interactions of tazobactam with beta-lactamases from all major structural classes." Antimicrobial agents and chemotherapy 37.4 (1993): 851-858.
Kurpiel, Philip M., and Nancy D. Hanson. "Point mutations in the inc antisense RNA gene are associated with increased plasmid copy number, expression of blaCMY-2 and resistance to piperacillin/tazobactam in Escherichia coli."Journal of antimicrobial chemotherapy (2011): dkr479.
Lister, Philip D., Andrea M. Prevan, and Christine C. Sanders. "Importance of beta-lactamase inhibitor pharmacokinetics in the pharmacodynamics of inhibitor-drug combinations: studies with piperacillin-tazobactam and piperacillin-sulbactam." Antimicrobial agents and chemotherapy 41.4 (1997): 721-727.
Thomson, K. S., et al. "Beta-lactamase production in members of the family Enterobacteriaceae and resistance to beta-lactam-enzyme inhibitor combinations." Antimicrobial agents and chemotherapy 34.4 (1990): 622-627.
Seetulsingh, Prema S., Lucinda MC Hall, and David M. Livermore. "Activity of clavulanate combinations against TEM-1 β-lactamase-producing Escherichia coli isolates obtained in 1982 and 1989." Journal of antimicrobial chemotherapy27.6 (1991): 749-759.
Alexov, Maria, Philip D. Lister, and Christine C. Sanders. "Efficacy of ampicillin-sulbactam is not dependent upon maintenance of a critical ratio between components: sulbactam pharmacokinetics in pharmacodynamic interactions." Antimicrobial agents and chemotherapy 40.11 (1996): 2468-2477.
Louie, Arnold, et al. "Pharmacodynamics of β-lactamase Inhibition by NXL104 in Combination with Ceftaroline, Examining Organisms with Multiple Types of β-lactamases." Antimicrobial agents and chemotherapy (2011): AAC-05005.
Bulik, Catharine C., et al. "In vivo comparison of CXA-101 (FR264205) with and without tazobactam versus piperacillin-tazobactam using human simulated exposures against phenotypically diverse gram-negative organisms."Antimicrobial agents and chemotherapy 56.1 (2012): 544-549.
Clinical and Laboratory Standards Institute CLSI Document M100-S22; Jan. 2012, vol. 32, No. 3 (33 pages).
Clinical and Laboratory Standards Institute CLSI Document M07-A9; Jan. 2012, vol. 32, No. 2 (88 pages).
European Committee on Antimicrob Sus Testing 2012.
Ge, Yigong, et al. "Pharmacokinetics and safety of CXA-101, a new antipseudomonal cephalosporin, in healthy adult male and female subjects receiving single-and multiple-dose intravenous infusions." Antimicrobial agents and chemotherapy 54.8 (2010): 3427-3431.
Juan, Carlos, et al. "Activity of a new antipseudomonal cephalosporin, CXA-101 (FR264205), against carbapenem-resistant and multidrug-resistant Pseudomonas aeruginosa clinical strains." Antimicrobial agents and chemotherapy 54.2 (2010): 846-851.
Titelman, Emilia, et al. "In vitro activity of CXA-101 plus tazobactam (CXA-201) against CTX-M-14—and CTX-M-15-producing Escherichia coli and Klebsiella pneumoniae." Diagnostic microbiology and infectious disease70.1 (2011): 137-141.
Jacqueline, Cédric, et al. "Efficacy of ceftolozane in a murine model of Pseudomonas aeruginosa acute pneumonia: in vivo antimicrobial activity and impact on host inflammatory response." Journal of Antimicrobial Chemotherapy68.1 (2013): 177-183.
Moyá, Bartolomé, et al. "Pan-β-lactam Resistance Development in Pseudomonas aeruginosa Clinical Strains: Molecular Mechanisms, PBPs Profiles and Binding Affinities." Antimicrobial agents and chemotherapy (2012): AAC-00680.
Chandorkar, Gurudatt, et al. "Intrapulmonary penetration of ceftolozane/tazobactam and piperacillin/tazobactam in healthy adult subjects."Journal of antimicrobial chemotherapy (2012): dks246.
Miller, Benjamin, et al. "Pharmacokinetics and safety of intravenous ceftolozane-tazobactam in healthy adult subjects following single and multiple ascending doses." Antimicrobial agents and chemotherapy 56.6 (2012): 3086-3091.
Moyá, Bartolomé, et al. "Affinity of the new cephalosporin CXA-101 to penicillin-binding proteins of Pseudomonas aeruginosa." Antimicrobial agents and chemotherapy 54.9 (2010): 3933-3937.
Livermore, David M., Shazad Mushtaq, and Yigong Ge. "Chequerboard titration of cephalosporin CXA-101 (FR264205) and tazobactam versus β-lactamase-producing Enterobacteriaceae." Journal of antimicrobial chemotherapy 65.9 (2010): 1972-1974.
Zamorano, Laura, et al. "Activity of the new cephalosporin CXA-101 (FR264205) against Pseudomonas aeruginosa isolates from chronically-infected cystic fibrosis patients." Clinical Microbiology and Infection 16.9 (2010): 1482-1487.
Riera, Elena, et al. "Anti-biofilm and resistance suppression activities of CXA-101 against chronic respiratory infection phenotypes of Pseudomonas aeruginosa strain PAO1." Journal of antimicrobial chemotherapy (2010): dkq143.
Moya, B., et al. "Activity of a new cephalosporin, 172 CXA-101 (FR264205), against beta-lactam-resistant Pseudomonas aeruginosa mutants selected 173 in vitro and after antipseudomonal treatment of intensive care unit patients."Antimicrobial 174 (2010): 1213-1217.
Bulik, Catharine C., Henry Christensen, and David P. Nicolau. "In vitro potency of CXA-101, a novel cephalosporin, against

(56) References Cited

OTHER PUBLICATIONS

Pseudomonas aeruginosa displaying various resistance phenotypes, including multidrug resistance." Antimicrobial agents and chemotherapy 54.1 (2010): 557-559.
Perletti et al. "CXA-101. Cephalosporin antibiotis." Drugs Fut, 2010. vol. 35, No. 12, pp. 977-986.
Livermore, David M., et al. "Activity of cephalosporin CXA-101 (FR264205) against Pseudomonas aeruginosa and Burkholderia cepacia group strains and isolates." International journal of antimicrobial agents 34.5 (2009): 402-406.
Giske et al., Activity of cephalosporin CXA-101 and comparators against extended-spectrum-{bela}-lactamase-producing Pseudomonas aeruginosa. J Antimicrob Chemother. 2009 ;64(2): 430-1.
Toda, Ayako, et al. "Synthesis and SAR of novel parenteral antipseudomonal cephalosporins: discovery of FR264205." Bioorganic & medicinal chemistry letters 18.17 (2008): 4849-4852.
Takeda et al., Stability of FR264205 against AmpC beta-lactamase of Pseudomonas aeruginosa. Int J Antimicrob Agents. Nov. 2007;30(5):443-5.
Jacqueline. In vivo Activity of CXA-101 against Pseudomonas aeruginosa in a Rabbit Experimental Pneumonia: Comparison with Ceflazidime Piperacillin-Tazobactam and Imipenem. 51st AnnualInterscience Conference on Antimicrobial Agents and Chemotherapy (ICAAC 2011); Sep. 17-20, 2011. Poster B-590.
Reynolds et al., Enterobacteriaceae in the UK and Ireland: Susceptibility to Old and New Agents. 52nd Annual Interscience Conference on Antimicrobial Agents and Chemotherapy (ICAAC 2012); Sep. 9-12, 2012. Poster C2-152.
Cabot et al. Dynamics and mechanisms of resistance development to ceflolozane, meropenem and ceflolozane-/tazobactam in wild-type and mutator P. aeruginosa strains. 52nd Annual Interscience Conference on Antimicrobial Agents and Chemotherapy (ICAAC 2012); Sep. 9-12, 2012. Poster C1-1970.
Melchers et al., In vitro Activity of CXA-101 Alone and in Combination With Tazobactam Against Extended Spectrum Beta-lactamase Harbouring Enterobacteriaceae. 52nd Annual Interscience Conference on Antimicrobial Agents and Chemotherapy (ICAAC 2012); Sep. 9-12, 2012. Poster F1-2008.
Ambrose, et al: Pharmacokinetic-pharmacodynamic considerations in the design of hospital-acquired or ventilator-associated bacterial pneumonia studies: look before you leap!; Clin Infect Dis, 2010, vol. 51, Suppl1, pp. S103-S110.
American Thoracic Society; Infectious Diseases Society of America; Guidelines for the management of adults with hospital-acquired, ventilator-associated, and healthcare-associated pneumonia; Am J Respir Grit Care Med., 2005, vol. 171(4), pp. 388-416.
Baughman, et al: The diagnosis and treatment challenges in nosocomial pneumonia; Diagn Microbiol Infect Dis, 1999, vol. 33(2), pp. 131-139.
Bergogne-Berezin: Predicting the efficacy of antimicrobial agents in respiratory infections: is tissue concentration a valid measure?; J Antimicrob Chemother, 1995, vol. 35, pp. 363-371.
Boselli, et al: Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.
Boselli, et al: Alveolar concentrations of piperacillin/tazobactam administered in continuous infusion to patients with ventilator-associated pneumonia; Grit Care Med, 2008, vol. 36, pp. 1500-1506.
Chastre, et al: Ventilator-associated pneumonia; Am J Respir Grit Care Med, 2002, vol. 165(7), pp. 867-903.
Chastre, et al: Comparison of 8 vs 15 days of antibiotic therapy for ventilator-associated pneumonia in adults: a randomized trial; JAMA, 2003, vol. 290(19), pp. 2588-2598.
El Solh: Update on the treatment of Pseudomonas aeruginosa pneumonia; J Antimicrob Chemother, 2009, vol. 64, pp. 229-238.
Ge, et al: Pharmacokinetics and safety of CXA-101, a new antipseudomonal cephalosporin, in healthy adult male and female subjects receiving single- and multiple-dose intravenous infusions; Antimicrob Agents Chemother, 2010, vol. 54, pp. 3427-3431.
Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.
Jones, et al: Microbial etiologies of hospital-acquired bacterial pneumonia and ventilator-associated bacterial pneumonia; Clin Infect Dis; 2010, Suppl1, pp. S81-S87.
Joseph, et al: Ventilator-associated pneumonia: A Review; Eur J Intern Med; 2010, vol. 21(5), pp. 360-368.
Klevens, et al: Estimating health care-associated infections and deaths in U.S. hospitals, 2002; Public Health Rep, 2007, vol. 122, pp. 160-166.
Knaus, et al: APACHE II: A severity of disease classification system; Grit Care Med, 1985, vol. 13, pp. 818-829.
Komuro, et al: Inhibition of the renal excretion oftazobactam by piperacillin; J Antimicrob Chemother, 1994, vol. 34, pp. 555-564.
Mesaros, et al: Pseudomonas aeruginosa: resistance and therapeutic options at the turn of the new millennium; Clin Microbiol Infect, 2007, vol. 13, pp. 560-578.
Miller, et al: Abstract: Probability of Target Attainment of CXA-201 in Patients with Renal Hyperclearance. 49th Annual Meeting of the Infectious Diseases Society of America (IDSA 2011); Oct. 20-23, 2011. Poster 81-589.
Occhipinti, et al: Pharmacokinetics and pharmacodynamics of two multiple-dose piperacillin-tazobactam regimens; Antimicrob Agents Chemother, 1997, vol. 41, pp. 2511-2517.
PEA: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.
Richards, et al: Nosocomial infections in medical intensive care units in the United States. National Nosocomial Infections Surveillance System; Grit Care Med, 1999, vol. 27(5), pp. 887-892.
Rodvold, et al: Penetration of anti-infective agents into pulmonary epithelial lining fluid: focus on antibacterial agents; Clin Pharmacokinet, 2011, vol. 50, pp. 637-664.
Schulgen, et al: Estimation of extra hospital stay attributable to nosocomial infections: heterogeneity and liming of events; J Clin Epidemiol; Apr. 2000, vol. 53(4), pp. 409-417.
Singh: et al: Short-course empiric antibiotic therapy for patients with pulmonary infiltrates in the intensive care unit. A proposed solution for indiscriminate antibiotic prescription; Am J Respir Grit Care Med, Aug. 2000, vol. 162(2, PI1), pp. 505-511.
Udy, et al: Augmented renal clearance: implications for antibacterial dosing in the critically ill; Clin Pharmacokinet, 2010, vol. 49(1), pp. 1-16.
Vincent, et al: Use of the SOFA score to assess the incidence of organ dysfunction/failure in intensive care units: results of a multicenter, prospective study. Working group on "sepsis-related problems" of the European Society of Intensive Care Medicine; Grit Care Med, 1998, vol. 26(11), pp. 1793-1800.
Wunderink, et al: Linezolid in methicillin-resistant *Staphylococcus aureus* nosocomial pneumonia: a randomized, controlled study; Clin Infect Dis, 2012, vol. 54(5), pp. 621-629.
Zilberberg, et al: Epidemiology of healthcare-associaled pneumonia (HCAP); Semin Respir Grit Care Med, 2009, vol. 30, pp. 10-15.
Lucasti: A Phase 3, Randomized, Double-Blind Study of Ceflobiprole Medocaril Versus Linezolid Plus Ceflazidime in the Treatment of Nosocomial Pneumonia; Ceflobiprole: Clinical Study Report Synopsis BAP00248/307; Issue Date: Jul. 14, 2010; Document No. EDMS-PSDB-6906024:3.0, (8 pages).
Pankey: Tigecycline; J Antimicrob Chemotherapy, 2005, vol. 56, pp. 470-480.
Freire, et al: Comparison of tigecycline with imipenem/cilastatin for the treatment of hospital-acquired penumonia; Diag Microbia and Infec Dis, 2010, vol. 68, pp. 140-151.
International Search Report, PCT/US2012/054191, dated May 2, 2013,4 pages.
Cubist Pharmaceuticals, Corporate Presentation, Feb. 26, 2010. 'Forward Looking Statement and Non-GAAP Financial Measure Disclosure,' slide 39 (1 page).

(56) References Cited

OTHER PUBLICATIONS

Cubist Pharmaceuticals, Corporate Presentation, Sep. 2011. 'Forward Looking Statement and Non-GAAP Financial Measure Disclosure,' slide 38 (1 pages).
Cubist Pharmaceuticals, "Cubist Pharmaceuticals to Acquire Calixa Therapeutics," Dec. 14, 2009, Available Online at http://Investors.cubisl.com/mobile/file.aspx?IID=4093793&FID=874771 (4 pages).
Shelley, S., "The Struggle to Get Anti-Infective on a Faster Track to Commercialization," Jan. 4, 2011, Available Online at http://pharmaceuticalcommerce.com/index.php?pg=special_report&articleid=2316 (5 pages).
Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.
Wv, Ri-na et al., 2009, "The Causes and Strategies for Ventilator-Associated Pneumonia", *Journal of Clinical Pulmonary Medicine*, 14(4):433-434.

Scheme 1

Scheme 2

METHODS FOR TREATING INTRAPULMONARY INFECTIONS

RELATED APPLICATIONS

This application is a continuation of U.S. patent application Ser. No. 13/607,138, filed Sep. 7, 2012, which claims priority to U.S. Provisional Application No. 61/532,914, filed Sep. 9, 2011, titled "Methods for Treating Intrapulmonary Infections," and U.S. Provisional Application No. 61/657,386, filed Jun. 8, 2012, titled "Methods for Treating Intrapulmonary Infections." The contents of any patents, patent applications, and references cited throughout this specification are hereby incorporated by reference in their entireties.

TECHNICAL FIELD

This disclosure relates to the treatment of intrapulmonary bacterial infections, including the treatment of nosocomial pneumonia infections, with a cephalosporin.

BACKGROUND

The cephalosporin (6R,7R)-3-[5-Amino-4-[3-(2-aminoethyl)ureido]-1-methyl-1H-pyrazol-2-ium-2-ylmethyl]-7-[2-(5-amino-1,2,4-thiadiazol-3-yl)-2-[(Z)-1-carboxy-1-methylethoxyimino]acetamido]-3-cephem-4-carboxylic acid (also referred to as "CXA-101" and previously designated FR264205) is an antibacterial agent. CXA-101 can be provided as the compound shown in FIG. 1. The antibacterial activity of CXA-101 is believed to result from its interaction with penicillin binding proteins (PBPs) to inhibit the biosynthesis of the bacterial cell wall which acts to stop bacterial replication. CXA-101 can be combined (e.g., mixed) with a β-lactamase inhibitor ("BLI"), such as tazobactam. Tazobactam is a BLI against Class A and some Class C β-lactamases, with well established in vitro and in vivo efficacy in combination with active β-lactam antibiotics. The combination of CXA-101 and tazobactam in a 2:1 weight ratio is an antibiotic pharmaceutical composition ("CXA-201") for parenteral administration. CXA-201 displays potent antibacterial activity in vitro against common Gram-negative and selected Gram-positive organisms. CXA-201 is a broad-spectrum antibacterial with in vitro activity against Enterobacteriaceae including strains expressing extended spectrum β-lactamases-resistant ($MIC_{90}$=1 mg/mL), as well as *Pseudomonas aeruginosa* (*P. aeruginosa*) including multi-drug resistant strains ($MIC_{90}$=2 μg/mL). CXA-201 is a combination antibacterial with activity against many Gram-negative pathogens known to cause intrapulmonary infections, including nosocomial pneumonia caused by *P. aeruginosa*.

Intrapulmonary infections, such as nosocomial pneumonia, remain a major cause of morbidity and mortality, especially infections caused by drug resistant pathogens such as *P. aeruginosa*. One challenge in treating intrapulmonary infections with systemic administration of an antibiotic is determining the antibiotic dose that will provide a therapeutically safe and effective concentration of the antibiotic at the site of an infection on the mucosal side of the bronchi in the lung (i.e., in the bronchial secretions). Many antibiotics diffuse poorly from the bloodstream across the bronchi [e.g., Pennington, J. E., "Penetration of antibiotics into respiratory secretions," *Rev Infect Dis* 3(1):67-73 (1981)], which can result in the administration of higher doses of antibiotic than would be prescribed for a truly systemic infection. Furthermore, the purulent sputum that characterizes infected patients tends to compromise the potency of many antibiotics (See e.g., Levy, J., et al., "Bioactivity of gentamicin in purulent sputum from patients with cystic fibrosis or bronchiectasis: comparison with activity in serum," *J Infect Dis* 148(6):1069-76 (1983)). In some cases, the result is the prescription of large amounts of a systemically administered antibiotic to treat an intrapulmonary infection.

The efficacy of an antibiotic depends in part on the concentration of the drug at the site of action. Efficacy of antimicrobial therapy requires adequate antibiotic concentrations at the site of bacterial infection, and some authorities believe that epithelial lining fluid (ELF) concentrations are a reasonable surrogate for predicting effective concentrations for treating intrapulmonary infections such as pneumonia. For many antibiotics, clinical data correlating ELF concentrations to clinical outcome is unavailable and the clinical significance of differences in pulmonary penetration of antibiotics is unknown or poorly characterized. Few studies have quantified the penetration of β-lactam agents into the lung, as measured by the ratio of area under the concentration-time curve (AUC) in ELF to AUC in plasma (AUC(ELF)/AUC(plasma) ratio). For some published studies, the concentration of antibiotics measured in the ELF of the lung has varied widely. For example, the reported penetration ratio of telavancin in healthy human volunteers ranges widely between 0.43 and 1.24 (Lodise, Gottfreid, Drusano, 2008 Antimicrobial Agents and Chemotherapy). Thus, predicting the penetration of a drug into the ELF a priori, based on the structure, molecular weight, size and solubility is difficult due to the limited data available on the effect of physicochemical properties on the lung penetration of drugs.

Accordingly, the efficacy of a particular drug in treating intrapulmonary infections, in particular nosocomial pneumonia, cannot be predicted solely on the basis of data, such as in vitro data relating to the activity of that drug against a particular bacterium, which does not give any indication as whether the drug will accumulate at a therapeutically safe and effective concentration at the site of an infection on the mucosal side of the bronchi in the lung (i.e., in the bronchial secretions). For instance, tigicycline, a glycylcycline antimicrobial, has in vitro activity against many species of Gram-positive and Gram-negative bacteria, including *P. aeruginosa*, and it has been approved by the FDA for the treatment of complicated skin and skin structure infections, complicated intra-abdominal infections, and community acquired pneumonia. However, tigicycline is not approved for the treatment of nosocomial pneumonia, in view of an increased mortality risk associated with the use of tigicycline compared to other drugs in patients treated for nosocomial pneumonia.

SUMMARY

The present invention provides methods for treating intrapulmonary infections, including nosocomial pneumonia, with systemic administration of a pharmaceutical composition comprising ceftolozane. The invention is based in part on results from a human clinical study designed to assess the ELF penetration of CXA-201 in comparison to piperacillin/tazobactam, indicated for the treatment of nosocomial pneumonia. The study described herein quantified the penetration of CXA-201 into the lung, as measured by the ratio of area under the concentration-time curve (AUC) in epithelial lining fluid (ELF) to AUC in plasma (AUC(ELF)/AUC (plasma) ratio). The results of the study indicate that CXA-201 penetrated into the ELF of human patients, with a ceftolozane ELF/plasma AUC ratio of 0.48. The measured ELF concentrations of ceftolozane exceeded 8 µg/mL for 60% of the 8-hour dosing interval, a concentration that is predicted to inhibit 99% of Pseudomonas aeruginosa based on current surveillance data.

The study showed that CXA-201 penetrated well into the ELF of healthy volunteers compared to piperacillin/tazobactam, an agent widely used for treatment of lower respiratory infections. The intrapulmonary pharmacokinetics measured in the study supports the use of CXA-201 as a parenteral (e.g., intravenous) antibiotic for treatment of intrapulmonary infections, such as nosocomial pneumonia or other lower respiratory tract infections.

DETAILED DESCRIPTION

Figure 1:
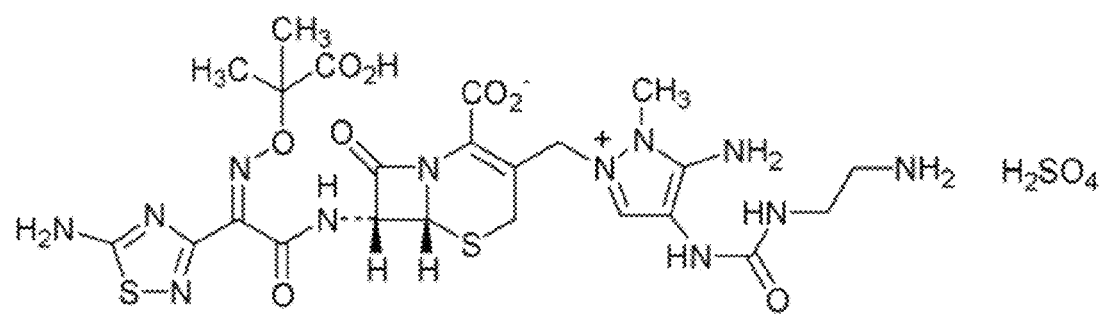
FIG. 1 is the chemical structure of a salt of ceftolozane hydrogen sulfate salt.

The present disclosure relates to the treatment of intrapulmonary infections, including nosocomial pneumonia, with systemic administration of a pharmaceutical composition comprising ceftolozane, including the parenteral administration of a therapeutically effective amount of a pharmaceutical composition comprising ceftolozane and tazobactam. As used herein, the term "ceftolozane" means CXA-101 in a free-base or salt form, preferably a hydrogen sulfate form (illustrated in FIG. 1). In one embodiment, ceftolozane is CXA-101 in its free-base form. In another embodiment, ceftolozane is CXA-101 in its salt form, preferably a hydrogen sulfate form.

In a preferred embodiment, ceftolozane (in free base or salt form, preferably hydrogen sulfate form) and tazobactam are in a 2:1 (ceftolozane:tazobactam) weight ratio. In a particular embodiment, provided herein are methods of treating intrapulmonary infections, including nosocomial pneumonia, with systemic administration of a pharmaceutical composition comprising ceftolozane hydrogen sulfate and tazobactam in a 2:1 weight ratio. The combination of ceftolozane hydrogen sulfate and tazobactam in a 2:1 weight ratio is referred to herein and in the examples as "CXA-201."

In one aspect, the invention provides a method of treating an intrapulmonary infection comprising administering a therapeutically effective amount of a pharmaceutical composition comprising ceftolozane. The method may comprise administering a pharmaceutical composition comprising ceftolozane in combination with tazobactam.

In another aspect, the invention provides a method of treating an intrapulmonary infection comprising the step of intravenously administering about every 8 hours to a subject in need thereof a pharmaceutical composition comprising 3.0 g of ceftolozane. The method may comprise administering a pharmaceutical composition comprising ceftolozane in combination with tazobactam. In one embodiment, the method comprises administering CXA-201 and the infection comprises Gram-negative bacteria. In another aspect, the invention provides a method of treating an intrapulmonary infection comprising the step of intravenously administering every 8 hours to a subject in need thereof a pharmaceutical composition comprising 3.0 g of ceftolozane.

In another aspect, the invention provides a method of providing tazobactam or ceftolozane in the epithelial lining fluid of a subject in an amount effective to treat an intrapulmonary infection, comprising the step of intravenously administering to the subject a pharmaceutical composition comprising ceftolozane. The method may comprise administering a pharmaceutical composition further comprising tazobactam, optionally wherein the pharmaceutical composition is CXA-201. The method may comprise administering about 1.5 g of ceftolozane and tazobactam in total every 8 hours. In one embodiment, the amount of the ceftolozane in the ELF of the subject effective to treat an intrapulmonary infection is at least about 8 µg/ml. The ELF concentration of ceftolozane in the ELF may reach at least about 8 µg/ml after administration of the pharmaceutical composition. The subject is typically a human having, or believed to be at risk of having, nosocomial pneumonia. The subject (or patient) may, in some embodiments, have ventilator acquired pneumonia or hospital acquired pneumonia.

In another aspect, the invention provides the use of ceftolozane in the manufacture of a medicament for the treatment of an intrapulmonary infection comprising administering a therapeutically effective amount of a pharmaceutical composition comprising the ceftolozane. The use may comprise administering the pharmaceutical composition comprising ceftolozane, in combination with tazobactam.

In another aspect, the invention provides the use of ceftolozane in the manufacture of a medicament for the treatment of an intrapulmonary infection comprising intravenously administering a pharmaceutical composition comprising 3.0 g of the ceftolozane every 8 hours to a subject in need thereof. The use may comprise administering the pharmaceutical composition comprising ceftolozane in combination with tazobactam. In one embodiment, the use comprises administering ceftolozane and tazobactam and the infection comprises Gram-negative bacteria.

In another aspect, the invention provides the use of ceftolozane in the manufacture of a medicament for the treatment of an intrapulmonary infection comprising intravenously administering a pharmaceutical composition comprising the ceftolozane, wherein tazobactam or ceftolozane is provided in the epithelial lining fluid of a subject in an amount effective to treat the intrapulmonary infection. The use may comprise administering a pharmaceutical composition further comprising tazobactam, optionally wherein the pharmaceutical composition is CXA-201. The use may comprise administering about 1.5 g of ceftolozane and tazobactam every 8 hours. In one embodiment, the amount of the ceftolozane in the ELF of the subject effective to treat an intrapulmonary infection is at least about 8 μg/ml. The ELF concentration of ceftolozane in the ELF may reach at least about 8 μg/ml after administration of the pharmaceutical composition. The subject is typically a human having, or believed to be at risk of having, nosocomial pneumonia. The subject (or patient) may, in some embodiments, have ventilator acquired pneumonia or hospital acquired pneumonia. In the methods and uses of the invention, the pharmaceutical composition may be administered parenterally. The pharmaceutical composition may be administered intravenously. In some embodiments, the pharmaceutical composition is intravenously administered about once every 8 hours as an infusion. The pharmaceutical composition may be intravenously administered as a 60-minute infusion.

In the methods and uses of the invention, the intrapulmonary infection may be an infection in the lung. The intrapulmonary infection may be pneumonia. In a preferred embodiment, the intrapulmonary infection is nosocomial pneumonia. The intrapulmonary infection may comprise *Pseudomonas aeruginosa*, Enterobacteriaceae, or a combination thereof. Typically, the intrapulmonary infection comprises *Pseudomonas aeruginosa*. The intrapulmonary infection may comprise a pathogen with minimum inhibitory concentration for CXA-201 of ≤8 μg/ml. The intrapulmonary infection may comprise a pathogen with minimum inhibitory concentration for ceftolozane of ≤8 μg/ml.

In another aspect, the invention provides ceftolozane, for use in a method of treating an intrapulmonary infection. In one embodiment, the ceftolozane is parenterally administered. Typically, the ceftolozane is intravenously administered. In some embodiments, the ceftolozane is administered about once every 8 hours as an infusion. In some embodiments, the ceftolozane is intravenously administered as a 60-minute infusion.

In one embodiment, the ceftolozane is for use in a method of treating an intrapulmonary infection wherein the intrapulmonary infection comprises an infection in the lung. The intrapulmonary infection may be pneumonia. In a preferred embodiment, the ceftolozane is for use in a method of treating nosocomial pneumonia. The intrapulmonary infection may comprise *Pseudomonas aeruginosa*, Enterobacteriaceae, or a combination thereof. Typically, the intrapulmonary infection comprises *Pseudomonas aeruginosa*. The intrapulmonary infection may comprise a pathogen with minimum inhibitory concentration for ceftolozane and tazobactam of ≤8 μg/ml. The intrapulmonary infection may comprise a pathogen with minimum inhibitory concentration for ceftolozane of ≤8 μg/ml.

The invention also provides ceftolozane, for use in a method of treating an intrapulmonary infection, comprising administration of ceftolozane in combination with tazobactam. In one embodiment, the ceftolozane and/or tazobactam is parenterally administered. Typically, the ceftolozane and/or tazobactam is intravenously administered. In some embodiments, the ceftolozane and/or tazobactam is administered about once every 8 hours as an infusion. In some embodiments, the ceftolozane and/or tazobactam is intravenously administered as a 60-minute infusion. In one embodiment, both the ceftolozane and tazobactam are parenterally administered. In another embodiment, both the ceftolozane and tazobactam are intravenously administered. In some embodiments, both the ceftolozane and tazobactam are administered about once every 8 hours as an infusion. In some embodiments, both the ceftolozane and tazobactam are intravenously administered as a 60-minute infusion. In one embodiment, the ceftolozane is for use in a method of treating an intrapulmonary infection wherein the intrapulmonary infection comprises an infection in the lung. The intrapulmonary infection may be pneumonia. In a preferred embodiment, the ceftolozane is for use in a method of treating nosocomial pneumonia. The intrapulmonary infection may comprise *Pseudomonas aeruginosa*, Enterobacteriaceae, or a combination thereof. Typically, the intrapulmonary infection comprises *Pseudomonas aeruginosa*. The intrapulmonary infection may comprise a pathogen with minimum inhibitory concentration for ceftolozane and tazobactam of ≤8 μg/ml. The intrapulmonary infection may comprise a pathogen with minimum inhibitory concentration for ceftolozane of ≤8 μg/ml.

In another aspect, the invention provides tazobactam, for use in a method of treating an intrapulmonary infection, comprising administration of tazobactam in combination with ceftolozane. In one embodiment, the tazobactam and/or ceftolozane is parenterally administered. Typically, the tazobactam and/or ceftolozane is intravenously administered. In some embodiments, the tazobactam and/or ceftolozane is administered about once every 8 hours as an infusion. In some embodiments, the tazobactam and/or ceftolozane is intravenously administered as a 60-minute infusion. In one embodiment, both the tazobactam and ceftolozane are parenterally administered. In another embodiment, both the tazobactam and ceftolozane are intravenously administered. In another embodiment, both the tazobactam and ceftolozane are administered about once every 8 hours as an infusion. In another embodiments, both the tazobactam and ceftolozane are intravenously administered as a 60-minute infusion.

In one embodiment, the tazobactam is for use in a method of treating an intrapulmonary infection wherein the intrapulmonary infection comprises an infection in the lung. The intrapulmonary infection may be pneumonia. In a preferred embodiment, the tazobactam is for use in a method of treating nosocomial pneumonia. The intrapulmonary infection may comprise *Pseudomonas aeruginosa*, Enterobacteriaceae, or a combination thereof. Typically, the intrapulmonary infection comprises *Pseudomonas aeruginosa*. The intrapulmonary infection may comprise a pathogen with minimum inhibitory concentration for ceftolozane and tazobactam of ≤8 μg/ml. The intrapulmonary infection may comprise a pathogen with minimum inhibitory concentration for ceftolozane of ≤8 μg/ml.

In another aspect, the invention provides ceftolozane and tazobactam, as a combined preparation for simultaneous, separate or sequential use in a method of treating an intrapulmonary infection. In one embodiment, the ceftolozane and tazobactam are parenterally administered. Typically, the ceftolozane and tazobactam are intravenously administered. In some embodiments, the ceftolozane and tazobactam are administered about once every 8 hours as an infusion. In some embodiments, the ceftolozane and tazobactam, are intravenously administered as a 60-minute infusion.

In one embodiment, the ceftolozane and tazobactam are for use in a method of treating an intrapulmonary infection wherein the intrapulmonary infection comprises an infection in the lung. The intrapulmonary infection may be pneumonia. In a preferred embodiment, the ceftolozane and tazobactam are for use in a method of treating nosocomial pneumonia. The intrapulmonary infection may comprise

*Pseudomonas aeruginosa*, Enterobacteriaceae, or a combination thereof. Typically, the intrapulmonary infection comprises *Pseudomonas aeruginosa*. The intrapulmonary infection may comprise a pathogen with minimum inhibitory concentration for ceftolozane and tazobactam of ≤8 µg/ml. The intrapulmonary infection may comprise a pathogen with minimum inhibitory concentration for ceftolozane of ≤8 µg/ml.

In another aspect, the invention provides ceftolozane for use in a method of providing tazobactam or ceftolozane in the epithelial lining fluid of a subject in an amount effective to treat an intrapulmonary infection, comprising the step of intravenously administering ceftolozane. In some embodiments, ceftolozane is administered in combination with tazobactam. Preferably, CXA-201 is administered. In preferred embodiments, about 1.5 g of ceftolozane and tazobactam is administered every 8 hours. In one embodiment, the amount of the ceftolozane in the ELF of the subject effective to treat an intrapulmonary infection is at least about 8 µg/ml. The ELF concentration of ceftolozane in the ELF may reach at least about 8 µg/ml after administration of the ceftolozane. The subject is typically a human having, or believed to be at risk of having, nosocomial pneumonia. The subject (or patient) may, in some embodiments, have ventilator acquired pneumonia or hospital acquired pneumonia.

The safe and effective treatment of intrapulmonary infection with CXA-201 includes administration of an amount of the CXA-201 selected to provide a therapeutically effective dose of the CXA-201 antibiotic in the epithelial lining fluid (ELF). The penetration of CXA-201 into the ELF compared to a piperacillin/tazobactam comparator was assessed in a Phase 1 clinical study in healthy adult volunteers. The piperacillin/tazobactam comparator contained piperacillin/tazobactam in an 8:1 weight ratio with a total of 2.79 mEq of sodium per gram of piperacillin, FDA approved under the tradename ZOSYN® ("Zosyn"). The study results evaluate the penetration of intravenously administered CXA-201 into healthy human lungs, as measured by the ratio of area under the concentration-time curve (AUC) in epithelial lining fluid (ELF) to AUC in plasma (AUC(ELF)/AUC(plasma) ratio).

In the study, a 4.5 g amount of piperacillin/tazobactam incorporates the same dose of tazobactam (0.5 g) as 1.5 g of CXA-201. A multiple-dose regimen was used in this study to ensure that the concentrations of the analytes reached steady-state in both plasma and ELF prior to assessment. Healthy volunteers were chosen to standardize the subject population and minimize the variability associated with using actively ill patients. The objectives of the study included: (1) determination and comparison of the ELF to plasma concentration ratios of multiple-doses of intravenous CXA-201 compared to piperacillin/tazobactam in healthy adult volunteers, and (2) assessment of the safety and tolerability of multiple-doses of intravenous CXA-201 in healthy adult volunteers.

The study was a Phase 1 prospective, randomized (1:1), comparator controlled, open-label study of 50 healthy adult volunteers. Each healthy volunteer received 3 doses of either CXA-201 (1.5 grams every 8 hours as a 60-minute infusion) or piperacillin/tazobactam (4.5 grams every 6 hours as a 30-minute infusion). Subjects received 3 doses of a study drug, underwent serial blood draws at planned plasma sampling timepoints, and underwent a single bronchoalveolar lavage (BAL) procedure at one of the scheduled timepoints (Table 1).

TABLE 1

| Plasma Sampling and BAL Timepoints | |
| --- | --- |
| Plasma Sampling Timepoints | BAL Timepoints |
| Intensive plasma sampling from all 25 subjects for one dosing interval | 5 subjects per timepoint per treatment group; in hours from start of the third infusion |
| CXA-201 | |
| 0 (pre-PK dose trough), 1, 2, 4, 6, 8 hours post start of infusion of the third dose of CXA 201 | 1, 2, 4, 6, 8 hours post start of infusion of the third dose of CXA 201 |
| Piperacillin/tazobactam | |
| 0 (pre-PK dose trough), 0.5, 1, 2, 4, 6 hours post start of infusion of the third dose of piperacillin/tazobactam | 0.5, 1, 2, 4, 6 hours post start of infusion of the third dose of piperacillin/tazobactam |

A total of 51 subjects were enrolled; 25 in the CXA-201 group and 26 in the piperacillin/tazobactam group. Key Inclusion Criteria for the study were: (1) healthy adult male or non-pregnant females between 18 and 50 years, inclusive; (2) body mass index between 18.5 and 30; and (3) forced Expiratory Volume in 1 second (FEV1)≥80%. Key Exclusion Criteria for the study were: (1) pregnancy or lactation; (2) clinically significant systemic disease or the existence of any surgical or medical condition that may have interfered with the distribution, metabolism, or excretion of CXA-201; (3) history of asthma or any restrictive or obstructive lung disease; (4) history of smoking or abuse of narcotics or alcohol; (5) positive test for human immunodeficiency virus, Hepatitis B surface antigen, or Hepatitis C antibodies; (6) any condition or situation where bronchoscopy was not advisable; and (7) impairment of renal function (CrCl<90 mL/min).

Determination of the ELF to Plasma Concentration Ratios of Multiple-Doses of Intravenous CXA-201 Compared to Piperacillin/Tazobactam in Healthy Adult Volunteers.

Plasma and BAL datapoints were used to construct one concentration-time profile in the ELF using the mean concentrations at each time point. After dosing, a single ELF sample was obtained by bronchoalveolar lavage (BAL) from each healthy volunteer at one of 5 scheduled time points (5 subjects/time point/treatment group). The ELF to plasma concentrations of multiple-doses was determined Serial plasma samples were collected pre- and post-treatment over a 6-hour (piperacillin/tazobactam) or 8-hour (CXA-201) time period. Urea levels in the plasma and BAL were used to calculate the ELF drug concentrations (see Table 1). Pharmacokinetic parameters for ELF were calculated by non-compartmental analysis using the mean concentrations at each time point. The intrapulmonary penetration of CXA-201 into the ELF was determined by dividing the ELF $AUC_0$-t by mean plasma $AUC_0$-t.

The concentration of CXA-201 and piperacillin/tazobactam in ELF were estimated from the concentration of drug in BAL fluid, the volume of BAL fluid collected, and the ratio of urea concentration in BAL fluid to that in plasma. Calculation of ELF volume was determined by the urea dilution method, using urea as an endogenous marker of ELF recovered by BAL. Concentration of CXA-201 and piperacillin/tazobactam in ELF was estimated from the concentration of drug in BAL fluid, the volume of BAL fluid collected, and the ratio of urea concentration in BAL fluid to that in plasma. The following formulas represent these calculations:

$$CXA\text{-}201(CXA/T) = [CXA/T]_{BAL} \times V_{BAL}/V_{ELF}$$

$[CXA/T]_{BAL}$ is the concentration of CXA-201 in BAL fluid; $V_{BAL}$ is the volume of aspirated BAL fluid (total); $V_{ELF}$ is $V_{BAL} \times [urea]_{BAL}/[urea]_{plasma}$, where $[urea]_{BAL}$ is the concentration of urea in the BAL fluid (supernatant) and $[urea]_{plasma}$ is the concentration of urea in the plasma specimens.

$$\text{Piperacillin/tazobactam} = [PIP/T]_{BAL} \times V_{BAL}/V_{ELF}$$

[PIP/T]BAL is the concentration of piperacillin/tazobactam in BAL fluid; $V_{BAL}$ is the volume of aspirated BAL fluid (total); $V_{ELF}$ is $V_{BAL} \times [urea]_{BAL}/[urea]_{plasma}$, where $[urea]_{BAL}$ is the concentration of urea in the BAL fluid (supernatant) and $[urea]_{plasma}$ is the concentration of urea in the plasma specimens.

No oral antibiotic therapy was permitted. Safety was monitored through the review of vital signs, laboratory and physical examinations and the occurrence of adverse events (AEs). Subjects who received three doses of study medication and had both BAL and plasma samples collected were included in the pharmacokinetic (PK) analysis population. All randomized subjects who received any dose (including partial doses) of study medication were included in the safety analysis population.

The results of the study (Table 2) indicate that CXA-201 penetrated well into ELF. The ceftolozane component of CXA-201 ELF/plasma AUC ratio was 0.48, compared to 0.26 for the piperacillin component of piperacillin/tazobactam. The ELF concentrations of ceftolozane exceeded 8 µg/mL for 60% of the 8-hour dosing interval. The plasma concentrations for ceftolozane were consistent with those seen previously at this dose.

Figure 2A:
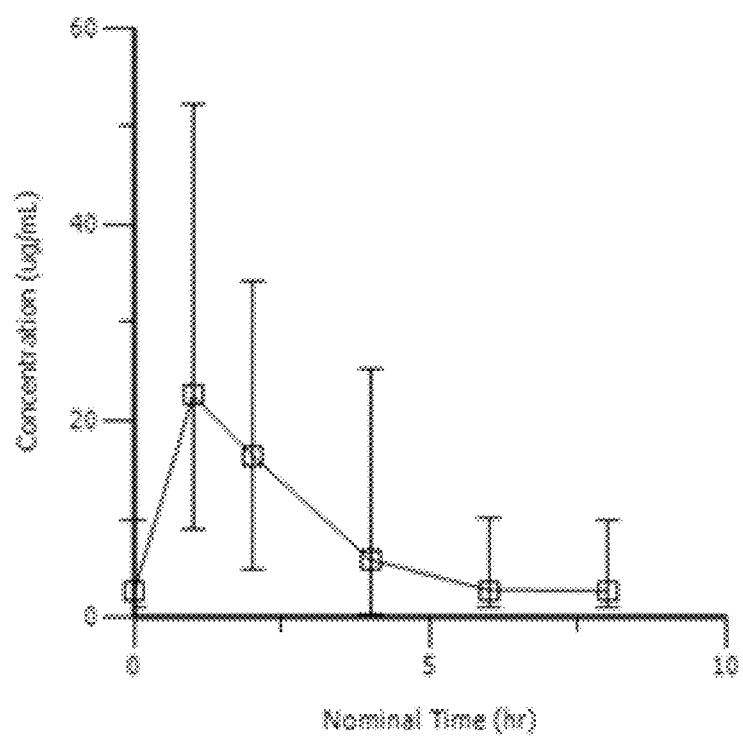
FIG. 2A is a graph showing the ELF Concentration vs. Time Profile for ceftolozane hydrogen sulfate salt (Median and Range) for CXA-201.
Figure 2B:
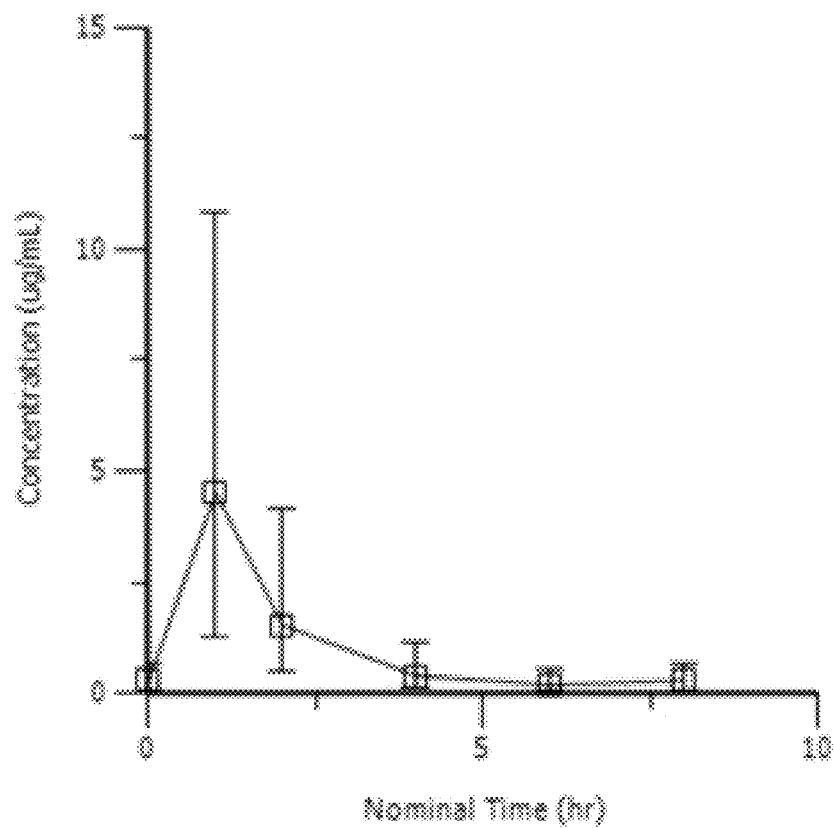
FIG. 2B is a graph showing the ELF Concentration vs. Time Profile for Tazobactam (Median and Range) for CXA-201.
Figure 3A:
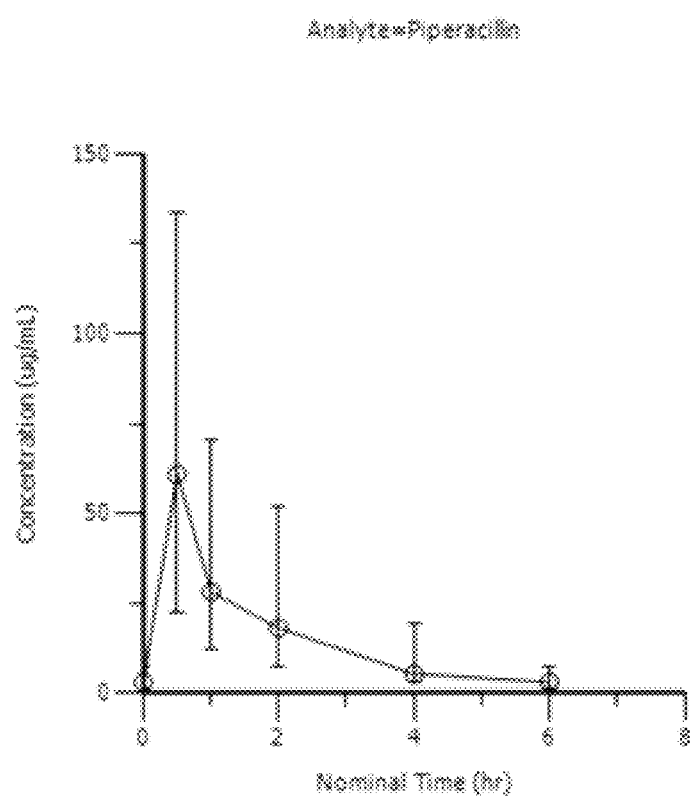
FIG. 3A is a graph showing the (Comparative) ELF Concentration vs. Time Profile for Piperacillin (Median and Range) for a piperacillin/tazobactam comparator (ZOSYN®).
Figure 3B:
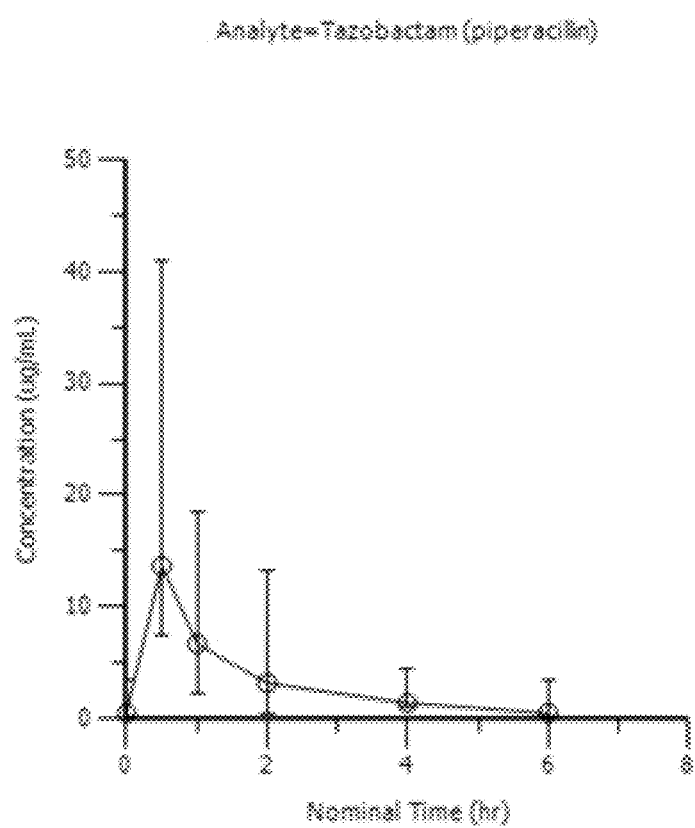
FIG. 3B is a graph showing the (Comparative) ELF Concentration vs. Time Profile for Tazobactam (Median and Range) for a piperacillin/tazobactam comparator (ZOSYN®).

The ELF concentration vs. time profiles for ceftolozane and tazobactam components of CXA-201 are shown in FIGS. 2A and 2B, respectively. Comparative data showing the ELF concentration vs. time profiles for piperacillin and tazobactam components of the comparator drug are shown in FIGS. 3A and 3B, respectively. The ELF to plasma penetration ratios are shown in Table 2.

The PK parameters were determined by non-compartmental PK analysis. PHOENIX® WinNonlin v 6.1 (PHARSIGHT®, Mountain View, Calif.) was used for the derivation of all PK individual measures for each subject. The PK parameters for ELF were calculated by taking the mean concentrations of the 5 subjects at each time point and constructing a single profile over the duration of sampling. In the event that the urea concentrations determined in plasma or ELF were below quantifiable limits, thereby providing only an estimate of concentration, those values were not used in the calculation of mean concentration at that time point. The ceftolozane, piperacillin, and tazobactam PK parameters that were computed in plasma and ELF were:

$C_{max}$ (µg/mL): Maximum plasma and ELF concentration over the entire sampling phase directly obtained from the experimental plasma concentration time data, without interpolation.

$T_{max}$ (hr): Sampling time at which $C_{max}$ occurred, obtained directly from the experimental plasma and ELF concentration time data, without interpolation.

$C_{last}$ (µg/mL): Plasma or ELF concentration when last quantifiable concentration was observed, relative to the end of infusion.

$T_{last}$ (hr): Time when the last quantifiable concentration was observed.

$AUC_{0-t}$ (µg*hr/mL): An area under the concentration time curve from the time of the dose to the end of the dosing interval.

Percent penetration into ELF: Calculated as the ratio of $AUC_{0-tELF}$ and mean $AUC_{0-tPlasma}$.

TABLE 2

Summary of ELF to Plasma Penetration Ratios

| Analyte | Mean Plasma $AUC_{0-\tau}$ (µg * hr/mL) | ELF $AUC_{0-\tau}$ (µg * hr/mL) | ELF Penetration Ratio |
|---|---|---|---|
| ceftolozane (in CXA-201) | 158.5 | 75.1 | 0.48 |
| Tazobactam (in CXA-201) | 19.3 | 8.5 | 0.44 |
| Piperacillin (in piperacillin/tazobactam) | 357.3 | 94.5 | 0.26 |
| Tazobactam (in piperacillin/tazobactam) | 46.1 | 24.7 | 0.54 |

The ELF/plasma AUC ratio for the ceftolozane component of CXA-201 was 0.48, compared to 0.26 for the piperacillin component of the comparator drug (piperacillin/tazobactam). The ELF/plasma AUC ratio for tazobactam was 0.44 and 0.54 when given as part of CXA-201 and piperacillin/tazobactam, respectively. The ELF concentrations of ceftolozane exceeded 8 µg/mL for 60% of the 8-hour dosing interval. The plasma and ELF concentrations of tazobactam when given as piperacillin/tazobactam was approximately 2-fold higher than when an equivalent dose was given as CXA-201.

The results show that ceftolozane and tazobactam (i.e., administered as CXA-201) penetrated well into the ELF of healthy volunteers compared to piperacillin/tazobactam, an agent widely used for treatment of lower respiratory infections. CXA-201's intrapulmonary pharmacokinetics support use of CXA-201 as a parenteral (e.g., intravenous) antibiotic for treatment of lower respiratory tract infections, including infections caused by pathogens with minimum inhibitory concentrations of ≤8 µg/ml. The concentrations of ceftolozane in ELF exceeded 8 µg/mL, a concentration that inhibits 99% of *P. aeruginosa*, for approximately 60% of the 8-hour dosing interval for the CXA-201 regimen of 1.5 grams every eight hours as a 60 minute infusion.

Assessment of the Safety and Tolerability of Multiple-Doses of Intravenous CXA-201 in Healthy Adult Volunteers Among the subjects, 50 of the 51 (98%) subjects received all 3 doses of study medication and completed the BAL procedure. One subject prematurely discontinued piperacillin/tazobactam and terminated their participation in the study due to an AE of hypersensitivity that occurred during administration of the first dose. Demographics and baseline characteristics are summarized in Table 3, the two treatment arms were well balanced.

TABLE 3

Demographics and Baseline Characteristics (Safety Population)

| | CXA-201 1.5 grams (N = 25) | Piperacillin/ tazobactam 4.5 grams (N = 26) |
|---|---|---|
| Sex, n (%) | | |
| Female | 11 (44.0) | 11 (42.3) |
| Male | 14 (56.0) | 15 (57.7) |
| Age, years | | |
| Mean (SD) | 32.6 (7.8) | 34.2 (8.5) |
| Minimum, Maximum | 21, 47 | 22, 49 |
| Race, n (%) | | |
| White | 20 (80.0) | 21 (80.8) |
| Black or African American | 2 (8.0) | 2 (7.7) |
| Asian | 1 (4.0) | 0 (0.0) |
| American Indian or Alaska Native | 0 (0.0) | 1 (3.8) |
| Native Hawaiian or Pacific Islander | 1 (4.0) | 0 (0.0) |
| Other | 1 (4.0) | 2 (7.7) |
| BMI, kg/m$^2$ | | |
| Mean (SD) | 26.21 (2.6) | 23.23 (2.4) |
| Minimum, Maximum | 22.3, 30.0 | 20.6, 29.9 |

During the study, treatment-emergent AEs (TEAEs) occurred in 20.0% (5/25) of subjects receiving CXA-201 and 23.1% (6/26) of subjects receiving piperacillin/tazobactam. No serious AEs were reported in either treatment group. All AEs were mild in severity. The incidence and pattern of AEs were generally similar in the 2 treatment groups, Table 4.

TABLE 4

TEAEs by Preferred Term (Safety Population)

| | | |
|---|---|---|
| Subjects with at least 1 TEAE | 5 (20.0) | 6 (23.1) |
| Diarrhea | 1 (4.0) | 3 (11.5) |
| Viral Upper Respiratory Infection | 1 (4.0) | 0 (0) |
| Musculoskeletal Chest Pain | 1 (4.0) | 0 (0) |
| Somnolence | 1 (4.0) | 0 (0) |
| Hematuria | 1 (4.0) | 0 (0) |
| Cough | 1 (4.0) | 0 (0) |
| Type I Hypersensitivity | 0 (0) | 1 (3.8) |
| Alanine Aminotransferase Increased | 0 (0) | 1 (3.8) |
| Aspartate Aminotransferase Increased | 0 (0) | 1 (3.8) |
| Blood Creatine Phosphokinase Increased | 0 (0) | 1 (3.8) |
| Hyperkalemia | 0 (0) | 1 (3.8) |

Eight subjects had TEAEs assessed as related to study drug; two in the CXA-201 group (diarrhea and somnolence in 1 subject each) and six in the piperacillin/tazobactam group (diarrhea in 3 subjects, type I hypersensitivity in 1 subject, blood creatine phosphokinase increased in 1 subject, and alanine aminotransferase increased, aspartate aminotransferase increased, and hyperkalaemia all in the same 1 subject). One piperacillin/tazobactam-treated subject discontinued study drug due to an adverse event, type I hypersensitivity. There were no clinically significant changes in safety laboratory assessments or vital signs.

CXA-201 appeared safe and well tolerated in this group of healthy adult subjects.

Determining Appropriate Dose

A Monte Carlo simulation was performed based on clinical trial data to predict an effective CXA-201 dose for treating nosocomial pneumonia using PHOENIX® NLME (PHARSIGHT®, Mountain View, Calif.) software, a tool for data processing and modeling for population PK/PD analysis. A population pharmacokinetic (PK) model was developed using the CXA-201 plasma concentration versus time data from a previously conducted Phase 2 study in patients with complicated intra abdominal infections. Estimates of clearance and volume of distribution along with the associated inter-individual variability were obtained from these analyses. The outputs from the PK population model served as inputs for a clinical trial simulation performed using PHARSIGHT® Trial Simulator (PHARSIGHT®) software, a tool for defining and testing interactive drug models, exploring and communicating study design attributes, and performing statistical and sensitivity analysis through graphical and statistical summaries. Based on the mean ELF penetration data, an ELF/Plasma AUC ratio of 0.48 for ceftolozane (modeled as a numerical range of 0.25-0.65) calculated from the ceftolozane ELF study mentioned above was used to generate a random/Plasma AUC ratio from the range 0.25-0.65 for each simulated patient. This range reflects a conservative estimate of the potential distribution in a patient population. Using the results from the PK population model and the ELF/Plasma AUC ratio, the model simulated plasma and ELF concentration of CXA-201 versus time profiles for 1,000 hypothetical clinical trial patients with nosocomial pneumonia. The model evaluated the probability of clinical success of the 3.0 g every 8 hour (q8 h) dose of CXA-201 against three key pathogens in nosocomial pneumonia. The MIC distribution for these pathogens was imputed from 2008 United States surveillance data. Clinical success was defined as the achievement of an ELF or plasma concentration of ceftolozane higher than the MIC(s) of the lower respiratory pathogen(s) for a given patient. In vivo models have demonstrated that, as for typical cephlaosporins, the relavent PK/PD driver for CXA-201 is the percentage of time above MIC during the dosing interval. The target is to achieve concentrations that exceed the MIC of the pathogen for 45-50% of the time between each q8H dose. Thus, a threshold of 50% time above the minimum inhibitory concentration [T>MIC] on Day 7 of treatment was used. Plasma and ELF concentrations were estimated at 15 time-points post-administration on Day 7 when dosed every 8 hours. The results of these simulations are shown in Table 5.

TABLE 5

Probability of Target Attainment versus Key Pathogens in Nosocomial Pneumonia Using the Simulated 3.0 g versus the 1.5 g Dose of Ceftolozane/tazobactam

| Pathogen | Dosing Regimen | 50% T > MIC in Plasma | 50% T > MIC in ELF |
|---|---|---|---|
| *P. aeruginosa* | 1.5 g q8h | 98.2 | 94.6 |
| | 3.0 g q8h | 99.4 | 98.5 |
| *E. coli* | 1.5 g q8h | 96.3 | 94.2 |
| | 3.0 g q8h | 98.8 | 95.5 |
| *K. pneumoniae* | 1.5 g q8h | 90.2 | 87.3 |
| | 3.0 g q8h | 92.6 | 89.3 |

Abbreviation:
T > MIC = Time above minimum inhibitory concentration.

These simulations demonstrate that the 3.0 g dose of CXA-201 administered every 8 hours is expected to provide adequate concentrations for treatment of the vast majority of lower respiratory infections caused by these pathogens.

Following these simulations, the safety and tolerability of a 10 day course of CXA-201 3.0 g IV q8 h was evaluated in healthy human volunteers. Subjects were randomized to receive either 3.0 g (2.0/1.0 g) CXA-201 (n=8), 1.5 g (1.0/0.5 g) CXA-201 (n=4), or placebo (n=4). The data showed that CXA-201 was generally safe and well tolerated in this study. There were no serious adverse events or deaths reported in this study.

In conclusion, given the pharmacokinetic simulations conducted, the favorable data from the intrapulmonary PK study and demonstrated safety and tolerability of the higher dose of CXA-201 in the Phase 1 study mentioned above, the data provide justification for the use of 3.0 g CXA-201 IV q8 h for the treatment of patients with nosocomial pneumonia caused by Gram-negative pathogens.

Preparing CXA-201

CXA-201 can be prepared by combining ceftolozane and tazobactam in a 2:1 weight ratio. CXA-201 can be obtained using methods described in U.S. Pat. No. 7,129,232 and Toda et al., "Synthesis and SAR of novel parenteral anti-pseudomonal cephalosporins: Discovery of FR264205," *Bioorganic & Medicinal Chemistry Letters*, 18, 4849-4852 (2008), incorporated herein by reference in its entirety.

Figure 4A:
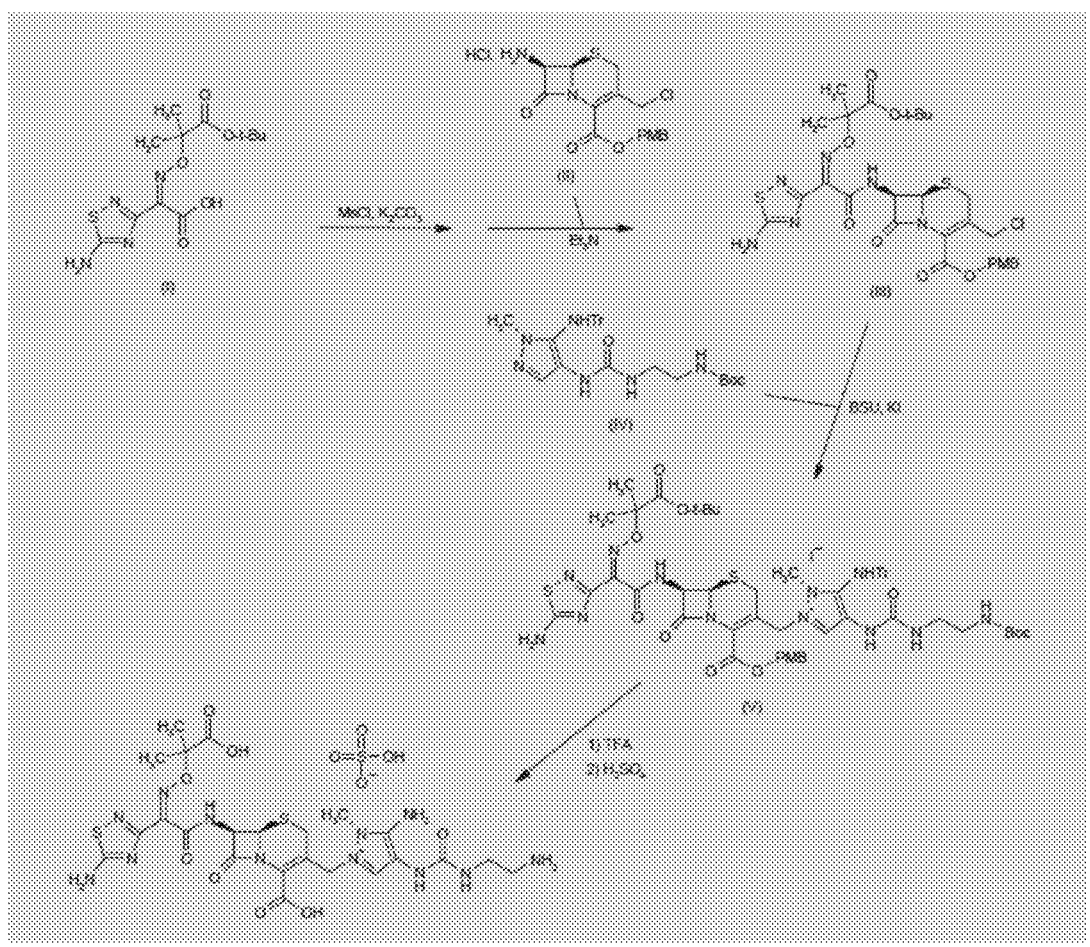
FIGS. 4A and 4B are synthetic schemes for preparing ceftolozane hydrogen sulfate salt.
Figure 4B:
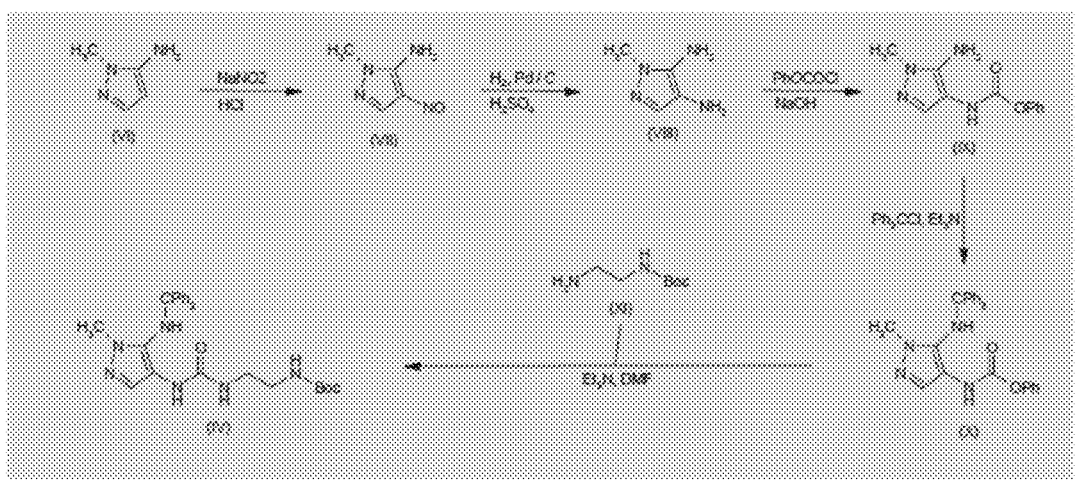

According to the method disclosed in Toda et al., "Synthesis and SAR of novel parenteral anti-pseudomonal cephalosporins: Discovery of FR264205," *Bioorganic & Medicinal Chemistry Letters*, 18, 4849-4852 (2008), ceftolozane can be obtained by the synthetic schemes of FIGS. 4A and 4B. Referring to FIGS. 4A and 4B, synthesis of ceftolozane can be performed via activation of the thiadiazolyl-oximinoacetic acid derivative (I) with methanesulfonyl chloride and $K_2CO_3$ in DMA at 10° C., followed by coupling with the 7-aminocephem (II) by means of $Et_3N$ in cold $EtOAc/H_2O$, affords amide (III) (1). Substitution of the allylic chloride of compound (III) with 4-RN-Boc-aminoethyl)carbamoylamino l-1-methyl-5-tritylaminopyrazole (IV) in the presence of 1,3-bis(trimethylsilyl)urea (BSU) and KI in DMF then affords the protected pyrazolium adduct (V), which, after full deprotection with trifluoroacetic acid in anisole/$CH_2Cl_2$, can be isolated as the hydrogensulfate salt by treatment with H2SO4 in i-PrOH/$H_2O$ (1, 2). Scheme 1. The pyrazolyl urea intermediate (IV) can be prepared as follows. Treatment of 5-amino-1-methylpyrazole (VI) with $NaNO_2$/HCl in water at 5° C. gives the 4-nitrosopyrazole derivative (VII), which can be reduced to the diaminopyrazole (VIII) by catalytic hydrogenation over Pd/C in the presence of $H_2SO_4$. Selective acylation of the 4-amino group of compound (VIII) with phenyl chloroformate in the presence of NaOH in $H_2O$/dioxane at 10° C. then yields the phenyl carbamate (IX). After protection of the free amine group of carbamate (IX) with chlorotriphenylmethane in the presence of $Et_3N$ in THF, the resulting N-trityl derivative (X) can be coupled with N-Boc-ethylenediamine (XI) in the presence of $Et_3N$ in DMF to afford pyrazolyl urea (IV).

Biological Activity Assay

The antibacterial activity of the CXA-201 or other compounds can be measured by the minimum inhibitory concentrations (MIC) of the compounds against various bacteria measured by using the broth microdilution method performed according to Clinical and Laboratory Standards Institute (CLSI) guidelines with modifications as described below (CLSI guidelines can be derived from the CLSI document M7-A8 published in January 2009: "Methods for Dilution Antimicrobial Susceptibility Tests for Bacteria That Grow Aerobically; Approved Standard-Eighth Edition").

To prepare for MIC testing, individual colonies can be isolated by streaking frozen glycerol material containing *Staphylococcus* or *Pseudomonas* spp. onto rich, non-selective, tryptic soy agar containing 5% sheep's blood (TSAB), and incubated at 37° C. for 18-24 hrs.

On the day of testing, primary cultures can be started by scraping off 5-10 colonies from the TSAB plates. The material can be suspended in ~5 mL of cation adjusted Mueller Hinton Broth (CAMHB) in 14 mL culture tubes and can be incubated at 37° C. with aeration (200 rpm) for ~2 hrs until the OD600 was ≥0.1.

Inoculum cultures can be prepared by standardizing the primary cultures to OD600=0.1 and then adding 20 μL of the adjusted primary culture per 1 mL CAMHB for *Pseudomonas* and CAMHB plus 4% NaCl for MRSA so that the final inoculum density was ~$10^5$ colony forming units per milliliter. Diluted inoculum cultures can be used to inoculate 50 μL per well in 96 well broth microdilution assay plates. 50 μL of CAMHB that contained compound concentrations ranging from 64-0.06 μg/mL in two-fold dilutions can also be added to the broth microdilution assay plates for a final volume 100 μL per well, therefore final culture $OD_{600}$ was approximately 0.001 and the final NaCl concentration for the MRSA strain was 2%.

Plates can be incubated for 18-20 hours at 37° C. with aeration (200 rpm). Following incubation, growth can be confirmed visually placing plates over a viewing apparatus (stand with a mirror underneath) and then $OD_{600}$ can be measured using a SpectraMax 340PC384 plate reader (Molecular Devices, Sunnyvale, Calif.). Growth was defined as turbidity that could be detected with the naked eye or achieving minimum $OD_{600}$ of 0.1. MIC values were defined as the lowest concentration producing no visible turbidity.

The examples and illustrative embodiments described herein are provided by way of illustration, and do not constitute additional limitations on the scope of the claims. While some embodiments have been shown and described in the instant specification, the specification as ready by one of ordinary skill in the relevant arts also discloses various modifications and substitutions of embodiments explicitly disclosed herein. The exemplary embodiments from the specification are not provided to read additional limitations into the claims.

The invention claimed is:

1. A method of treating an infection selected from the group consisting of: nosocomial pneumonia, ventilator acquired pneumonia and hospital acquired pneumonia, the method comprising repeatedly intravenously administering 2.0 g of ceftolozane and 1.0 g of tazobactam to a subject in need thereof about once every 8 hours.

2. The method of claim 1, wherein the method comprises administering the ceftolozane as a 60-minute infusion.

3. The method of claim 1, wherein the ceftolozane is a hydrogen sulfate salt.

4. The method of claim 1, wherein the ceftolozane and tazobactam are administered as a single pharmaceutical composition.

5. The method of claim 4, wherein the method comprises administering the pharmaceutical composition as a 60-minute infusion.

6. The method of claim 1, wherein the pneumonia is nosocomial pneumonia.

7. The method of claim 1, wherein the pneumonia is ventilator acquired pneumonia.

8. The method of claim 1, wherein the pneumonia is hospital acquired pneumonia.

9. The method of claim 1, wherein the ceftolozane is administered in its free base form.

10. The method of claim 1, wherein the ceftolozane is administered in its salt form.

11. The method of claim 6, wherein the ceftolozane is administered in its free base form.

12. The method of claim 6, wherein the ceftolozane is administered in its salt form.

13. The method of claim 1, wherein the infection comprises one or more pathogens selected from the group consisting of: *Pseudomonas aeruginosa, E. coli* and *K. pneumoniae*.

\* \* \* \* \*